United States Patent [19]

Hearn et al.

[11] Patent Number: 5,628,880
[45] Date of Patent: May 13, 1997

[54] ETHERIFICATION—HYDROGENATION PROCESS

[75] Inventors: Dennis Hearn; Gary R. Gildert, both of Houston; Willibrord A. Groten, Pasadena, all of Tex.

[73] Assignee: Chemical Research & Licensing Company, Pasadena, Tex.

[21] Appl. No.: 600,251

[22] Filed: Feb. 12, 1996

[51] Int. Cl.$^6$ ............................ B01D 3/34; B01J 8/00
[52] U.S. Cl. ........................... 203/29; 203/45; 203/56; 203/87; 203/DIG. 6; 422/193; 568/694; 568/697; 585/468
[58] Field of Search ........................ 203/29, 45, 56, 203/87, DIG. 6; 422/193; 568/697, 694; 585/468

[56] References Cited

U.S. PATENT DOCUMENTS

| | | | |
|---|---|---|---|
| 4,218,011 | 8/1980 | Smith, Jr. | 252/426 |
| 4,221,653 | 9/1980 | Chervenak et al. | 208/8 LE |
| 4,232,177 | 11/1980 | Smith, Jr. | 585/324 |
| 4,302,350 | 11/1981 | Smith, Jr. | 252/246 |
| 4,307,254 | 12/1981 | Smith, Jr. | 568/697 |
| 4,361,422 | 11/1982 | Derrien et al. | 44/56 |
| 4,490,481 | 12/1984 | Boitiaux et al. | 502/334 |
| 4,504,687 | 3/1985 | Jones, Jr. | 568/697 |
| 4,533,779 | 8/1985 | Boitiaux et al. | 585/259 |
| 4,550,012 | 10/1985 | Penick | 422/106 |
| 4,724,274 | 2/1988 | Boitiaux et al. | 585/668 |
| 4,740,633 | 4/1988 | Boitiaux et al. | 568/699 |
| 4,774,375 | 9/1988 | Hammershaimb | 585/251 |
| 4,925,989 | 5/1990 | Hagan et al. | 568/697 |
| 4,978,807 | 12/1990 | Smith, Jr. | 568/697 |
| 5,073,236 | 12/1991 | Gelbein et al. | 203/29 |
| 5,118,873 | 6/1992 | Smith, Jr. | 568/697 |
| 5,120,403 | 6/1992 | Smith, Jr. | 203/1 |
| 5,248,836 | 9/1993 | Bakshi et al. | 568/697 |
| 5,248,837 | 9/1993 | Smith, Jr. et al. | 568/697 |
| 5,313,005 | 5/1994 | Smith, Jr. et al. | 568/697 |
| 5,431,888 | 7/1995 | Hickey et al. | 422/191 |
| 5,510,568 | 4/1996 | Hearn | 585/834 |

FOREIGN PATENT DOCUMENTS

| | | |
|---|---|---|
| 0087980 | 9/1983 | European Pat. Off. . |
| 835689 | 5/1960 | United Kingdom . |
| 920012 | 3/1963 | United Kingdom . |

OTHER PUBLICATIONS

Boitiaux, et al, "Newest Hydrogenation Catalyst", *Hydrocarbon Processing*, Mar. 1985, pp. 51–59.

Derriou, et al "The IFP Selective Hydrogenation Process", *Chemical Engineering Progress*, Jan. 1974, pp. 74–80.

Cameron, et al "New Processes for Upgrading C4 and C5 Olefins Stream", Refining Symposium at Progue Czech Rep., Aug. 1994.

Barchas, et al "Combine Selective Hydrogenation and Distillation to Upgrade $C_4$ and $C_5$ Streams", *Fuel Reformation*, Sep./Oct. 1993 pp. 44–52.

*Primary Examiner*—Nina Bhat
*Attorney, Agent, or Firm*—Kenneth H. Johnson

[57] ABSTRACT

A process for removing dienes from etherification uses a hydrogenation zone in the reactor distillation column above the etherification zone. MTBE is produced and the unreacted $C_4$ stream is also subjected to selective hydrogenation of the butadiene contained in the $C_4$ feed stream. The $C_4$ stream is first contacted with methanol in the etherification zone where the MTBE is distilled downward. The unreacted $C_4$'s then are subjected to selective hydrogenation in the hydrogenation zone where butadiene in the overhead raffinate is reduced by over 90%. The hydrotreated $C_4$'s are thus suitable for cold acid alkylation or other use wherein butadiene is harmful.

17 Claims, 2 Drawing Sheets

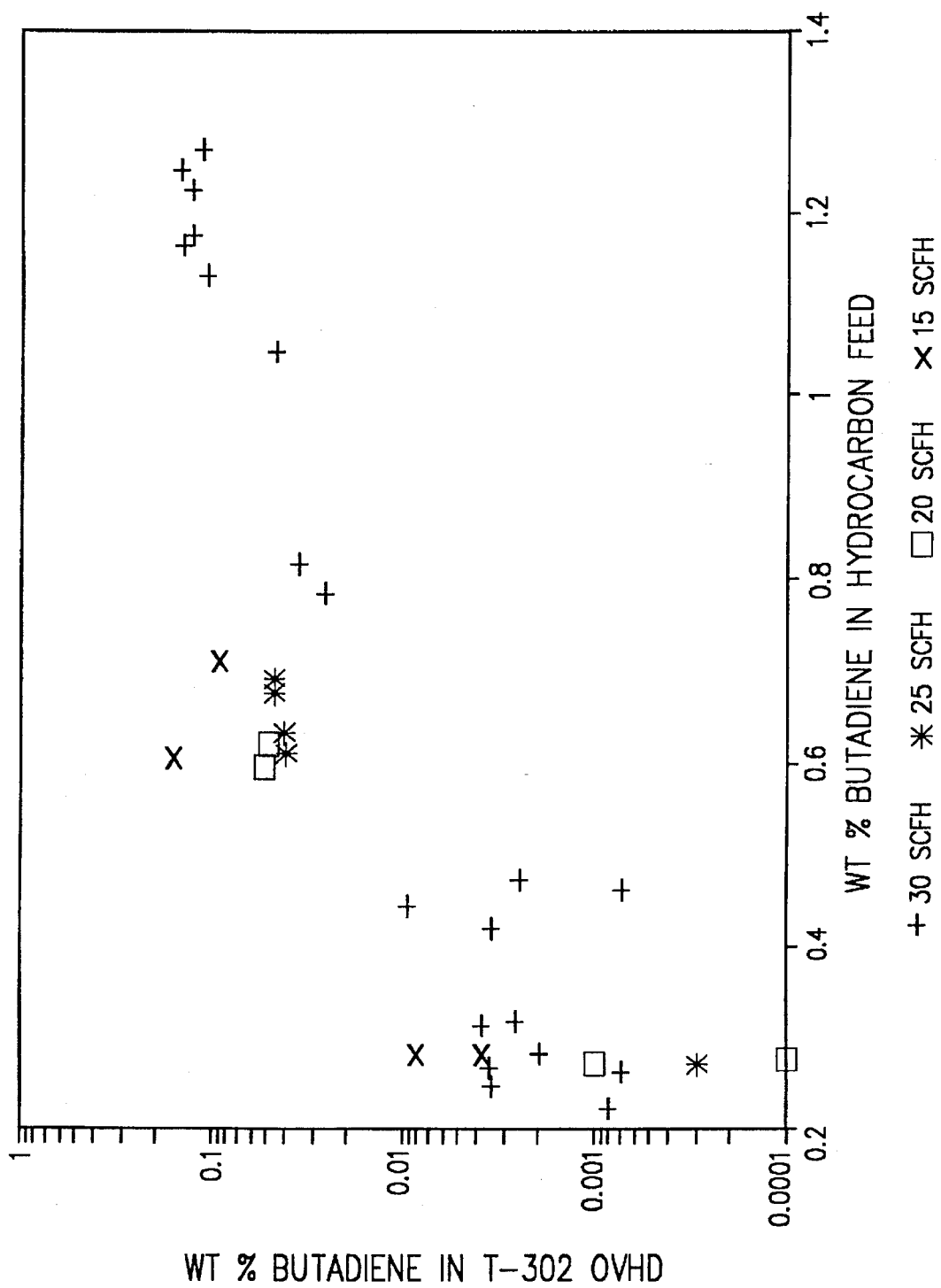

ETHERIFICATION—HYDROGENATION PROCESS

BACKGROUND OF THE INVENTION

1. Field of the Invention

The present invention relates to a catalytic distillation process for producing tertiary alkyl ethers wherein the unreacted raffinate is substantially free of butadiene and more attractive for use in cold acid alkylation processes and other processes.

2. Related Information

The production of tertiary alkyl ethers by the reaction of primary alcohol and an isoolefin is well known in the art. The use of a distillation column reactor to simultaneously react and distill the product from the reactants has been found to be especially beneficial in this normally equilibrium limited reaction. The description of the process using the distillation column reactor and variations thereon are disclosed in commonly assigned U.S. Pat. Nos. 4,218,011; 4,232,177; 4,305,254; 4,504,687; 4,978,807; 5,118,873; 5,120,403; 5,248,836; 5,248,837; and 5,313,005. Catalytic distillation has been widely applied to etherification of isoolefins, which is described in several of the noted patents.

U.S. Pat. No. 5,431,888 discloses a multi-purpose distillation column reactor wherein a hydrogenation catalyst for hydrotreating an isoolefin containing light naphtha from a fluid catalytic cracking unit to remove diolefins and mercaptans is stacked below an etherification catalyst.

Normally the olefin feed to a methyl tertiary butyl ether (MTBE) process is a mixed $C_4$ stream containing normal and iso butanes, normal and iso butenes and some butadiene. The isobutene ($iC_4^=$) preferentially react with methanol to form the MTBE with the remainder being essentially inert. The unreacted $C_4$'s are frequently used as feed stock to a cold acid alkylation process which reacts the normal butenes with isobutane to form isooctane. While butadiene at the levels used does not affect the etherification, any butadiene in the feed to the alkylation process reacts to form a sludge and results in unwanted "acid consumption". It would thus be highly desirable that raffinate from a $iC_4^=$ etherification be substantially free of butadiene. Also, skeletal isomerization of normal $C_4$ olefins to isobutene normally requires removal of butadiene.

The particular feature of the present invention is the discovery that the presence of methanol in the hydrogenation zone does not adversely affect the hydrogenation of the dienes and sequence of catalysts.

SUMMARY OF THE INVENTION

The present invention relates to a process wherein a distillation column reactor is used with a hydrogenation catalyst prepared as a distillation structure in a distillation column reactor downstream of an etherification reaction. Preferably the hydrogenation is carried out in a bed stacked above an etherification catalyst prepared as a distillation structure wherein isoolefins are preferentially reacted with alcohol in the lower etherification bed and dienes are hydrogenated with hydrogen in the upper hydrogenation bed. The hydrogenation, contrary to expectations was not inhibited by methanol in the hydrogenation zone. Methanol in azeotropic or in excess (usually less than 10% excess) thereof may be present in the hydrogenation zone with no appreciable detriment to the hydrogenation of the dienes.

In a preferred embodiment the invention is a catalytic distillation process for the production of methyl tertiary butyl ether (MTBE) from the reaction of reactants comprising isobutene in $C_4$ streams containing normal butenes, butanes and butadiene and methanol (MeOH) by feeding a mixture of the reactants into the reaction distillation column, below a bed of acid ion exchange resin catalyst which constitutes a first reaction distillation zone. Hydrogen may be fed to the distillation column reactor along with the mixed methanol/$C_4$ feed.

In the first (lower) reaction distillation zone the methanol preferentially reacts with the isobutene to form MTBE which is simultaneously distilled downward out of the bed. The unreacted and inert $C_4$'s are then boiled upward into a second (upper) reaction distillation zone containing a hydrogenation catalyst as a distillation structure wherein the butadiene is preferentially reacted with hydrogen to produce butenes and butanes. Surprisingly azeotropic concentrations of methanol in the $C_4$'s (about 4%) do not affect the butadiene conversion after the catalyst has been activated.

Quite surprisingly the low hydrogen partial pressure used in the distillation system did not result in the failure of the hydrogenation which would have been expected based on the high hydrogen partial pressure found in the liquid phase systems which are the world wide standard. The phenomenon of condensation which is a constant factor in a distillation is believed to result in the same or better hydrogen availability, as the high pressure in the liquid phase, that is, the hydrogen is introduced into the liquid so that the hydrogenation occurs.

The etherification feed may contain $C_4$ to $C_6$ isoolefins, usually butenes and amylenes and the alcohol may be $C_1$ to $C_4$ monools, preferably methanol and ethanol. The dienes are impurities, usually less than 1 wt. %, and usually those corresponding to the hydrocarbon feed cut.

Although it is preferred that the etherification is also a catalytic distillation reaction, the effluent from any etherification reactor, such as a straight pass liquid phase reactor or a boiling reactor can be fed directly to a distillation reactor containing the catalytic distillation hydrogenation zone, preferably to a conventional distillation zone below the hydrogenation zone. The conventions distillation zone may be contained in a separate unit and the overhead fed to the hydrogenation zone.

BRIEF DESCRIPTION OF THE DRAWINGS

FIG. 2 is graph showing hydrogenation performance at various levels of hydrogen feed rate and butadiene concentration.

DESCRIPTION OF THE PREFERRED EMBODIMENT

Figure 1:
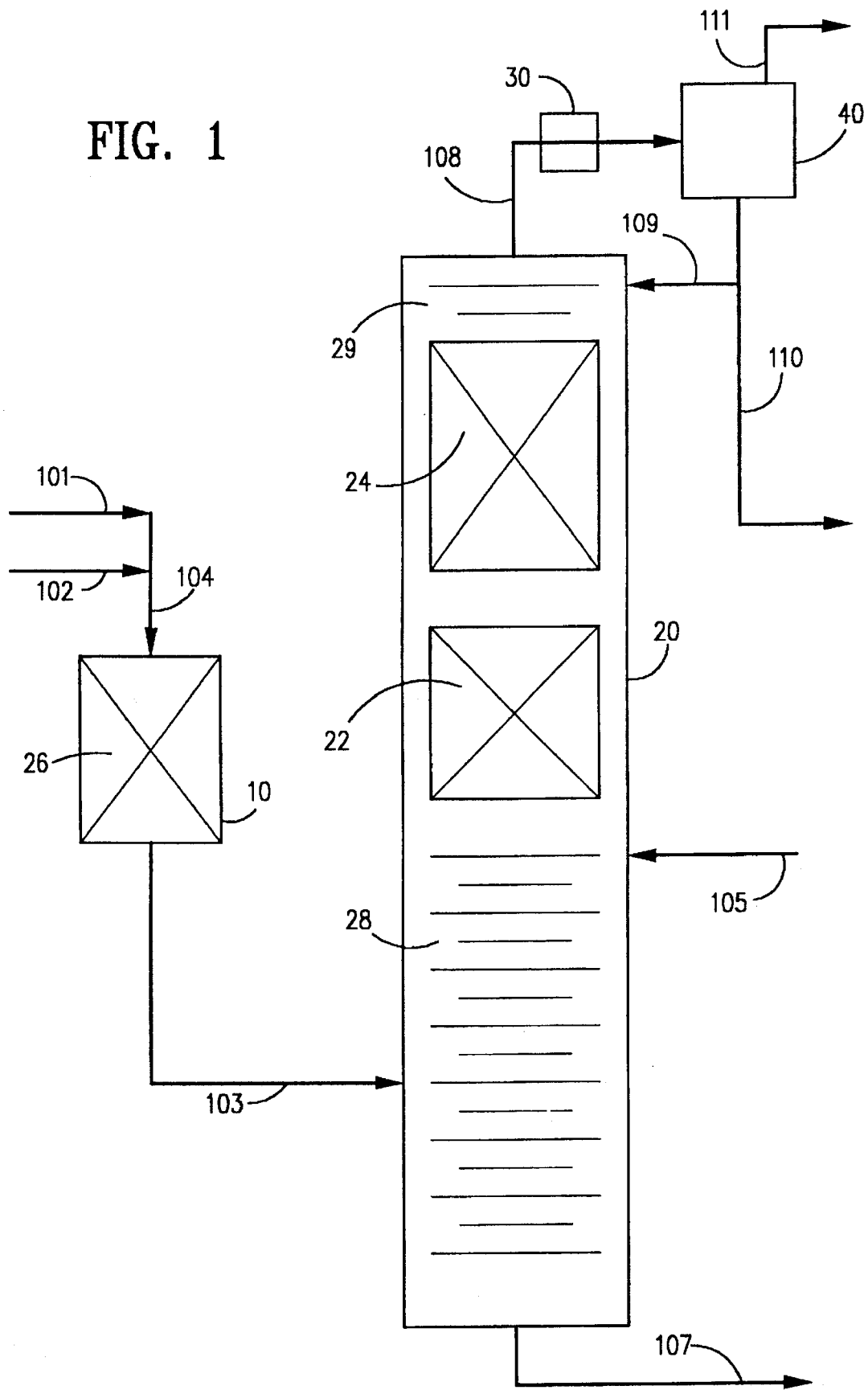
FIG. 1 is a simplified flow diagram in schematic form of a process embodying the present invention.

A preferred embodiment is a process for the production of methyl tertiary butyl ether and hydrogenation of the butadiene contained in the $C_4$ stream used for the etherification, comprising the steps of:

(a) feeding a first stream containing isobutene and butadiene, a second stream containing methanol and a third stream containing hydrogen to a distillation column reactor into a feed zone;

(b) contacting the streams in an etherification reaction distillation zone containing an etherification catalyst to concurrently:

(i) preferentially react at least a portion of the isobutene with a portion of the methanol to form methyl tertiary butyl ether, (ii) distill the methyl tertiary butyl ether downward out of the etherification reaction distillation zone and (iii) distill the unreacted isobutene, methanol, butadiene and hydrogen upward out of the etherification reaction distillation zone;

(c) contacting the unreacted isobutene, methanol, butadiene and hydrogen in a hydrogenation reaction distillation zone containing a hydrogenation catalyst to selectively hydrogenate a portion of the butadiene to butenes;

(d) withdrawing ether product from the distillation column reactor as bottoms; and (e) withdrawing an overheads stream from the distillation column reactor having a reduced butadiene content as compared to the butadiene content of the first stream.

In the hydrogenation reaction as in the etherification reaction, catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled at the boiling point of the mixture at the system pressure. The heat of reaction simply creates more boil up, but essentially no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux over the range of 0.4 to 5 L/D (wt. of liquid just below the catalyst bed/wt. distillate) gives excellent results.

The catalyst for the etherification is preferably an acidic cation exchange resin such as Amberlyst 15 as supplied by Rohm and Haas Chemical Company. A suitable catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalysts. The cloth may be any material which is inert in the reaction. Cotton or linen are useful, but fiber glass cloth or "Teflon" cloth are preferred.

Hydrogenation is the reaction of hydrogen with a carbon-carbon multiple bond to "saturate" the compound. This reaction has long been known and is usually done at super atmospheric pressures and moderate temperatures using a large excess of hydrogen over a metal catalyst. Among the metals known to catalyze the hydrogenation reaction are platinum, rhenium, cobalt, molybdenum, nickel, tungsten and palladium. Generally, commercial forms of catalyst use supported oxides of these metals. The oxide is reduced to the active form either prior to use with a reducing agent or during use by the hydrogen in the feed. These metals also catalyze other reactions, most notably dehydrogenation at elevated temperatures. Additionally they can promote the reaction of olefinic compounds with themselves or other olefins to produce dimers or oligomers as residence time is increased.

Selective hydrogenation of hydrocarbon compounds has been known for quite some time. Peterson, et al in "The Selective Hydrogenation of Pyrolysis Gasoline" presented to the Petroleum Division of the American Chemical Society in September of 1962, discusses the selective hydrogenation of $C_4$ and higher diolefins. Boitiaux, et al in "Newest Hydrogenation Catalyst", *Hydrocarbon Processing, March 1985*, presents a general, non enabling overview of various uses of hydrogenation catalysts, including selective hydrogenation of a propylene rich stream and other cuts. Conventional liquid phase hydrogenations as presently practiced requires high hydrogen partial pressures, usually in excess of 200 psi and more frequently in a range of up to 400 psi or more. In a liquid phase hydrogenation the hydrogen partial pressure is essentially the system pressure.

The preferred hydrogenation catalyst is an alumina supported palladium catalyst having a palladium content of about 0.5 wt %. The hydrogenation catalyst is generally supplied in the form of small spheres or extrudates of from 1/32 to 1/4 inches in diameter. A preferred catalyst structure for the present hydrogenation reaction comprises flexible, semi-rigid open mesh tubular material, such as stainless steel wire mesh, filed with a particulate catalytic material in one of several embodiments recently developed in conjunction with the present process. Most particularly the structure described in U.S. Pat. No. 5,431,890 which is herein incorporated by reference is preferred for the hydrogenation catalyst structure. Disclosed therein is a bale shaped catalytic distillation structure formed by placing multiple link or continuous tube shaped structures on top of a wire mesh screen, such as demister wire, arrayed at an angle to the longitudinal axis of the bale, such that when the wire mesh screen is rolled up, the rolled structure provides a new and improved catalytic distillation structure. The tube comprises flexible, semi-rigid open mesh tubular element filled with a particulate catalytic material, the tube shaped structure having a fastener every 1–12 inches in length to form a multiple link.

The hydrogen stream at an effectuating hydrogen partial pressure of at least about 0.1 psia to less than 70 psia, preferably less than 50 psia is conveniently fed to the reaction distillation column along with the other reactants. Within the hydrogen partial pressures as defined no more hydrogen than necessary to hydrogenate the highly unsaturated compounds (dienes) is employed, since the excess hydrogen is usually vented. This preferably is a hydrogen partial pressure in the range of about 0.1 to 10 psia and even more preferably no more than 7 psia. Optimal results have been obtained in the range between 0.5 and 5 psig hydrogen partial pressure.

One of the advantages to the instant process is that $C_4$'s from a fluid catalytic cracking unit (FCCU) may be used without pretreatment. This $C_4$ stream contains about 13.28 wt % isobutene, with up to 0.5 wt % butadiene. The remainder of the stream is essentially butanes and normal butenes.

Referring now to the FIG. 1 one preferred embodiment is described in more detail. The reactor 10 is preferably operated as the reactor described in U.S. Pat. No. 4,950,803, although any preliminary reactor configuration or no preliminary reactor at all may be used. Methanol is fed via flow line 101 and the FCCU $C_4$'s are fed via flow line 102, both being combined in flow line 104 and fed to a fixed bed down flow guard reactor 10 containing a bed of the acid cation exchange resin 26.

The effluent from the reactor 10 is taken via flow line 103 and fed to the distillation column reactor 20. The distillation column reactor 20 has a stripping section 28 below an etherification reaction distillation zone 22 containing the acid cation exchange resin distillation structure which in turn is below a hydrogenation reaction distillation zone 24 which contains the hydrogenation catalytic distillation structure. The column also includes a rectification section 29 above the hydrogenation zone 24. Hydrogen is fed via flow line 105 in feed line to column 20 below the catalyst containing zones, and thus is mixed with the other reactants before entering the hydrogenation zone 24.

The isobutene preferentially reacts with methanol in the etherification reaction distillation zone 22 to form methyl tertiary butyl ether which is higher boiling than either the $C_4$'s or the methanol and so is distilled downward into the stripping section 28 where any $C_4$'s and methanol are boiled back up into the etherification reaction distillation zone 22 for further reaction.

The unreacted $C_4$'s and an azeotrope of methanol (about 4%) are boiled upward into the hydrogenation reaction distillation zone 24 wherein the butadiene reacts with the hydrogen to reduce butadiene content to about 20–100 wppm.

Ether is withdrawn from the distillation column reactor 20 as bottoms via flow line 107. The overheads contain mostly unreacted $C_4$'s but having less than about 100 wppm of butadiene. When the distillation column reactor first comes on line the methanol concentration in the hydrogenation zone 24 was kept below about 2 wt % until the hydrogenation catalyst is activated. After the hydrogenation catalyst was activated the concentration was allowed to rise to the azeotropic level of 4 wt %. The activation time period must be determined for each individual catalyst.

The overheads are taken via flow line 108 and the C4's are condensed in the condenser 30 and collected in the receiver 40 where any uncondensed material is separated and taken via flow line 111. A portion of the $C_4$'s can be returned to the column as reflux via flow line 109 or taken as product via flow line 110. The overhead $C_4$ stream contains less than about 100 wppm of butadiene and in some cases only about 20 wppm. Generally the overhead products are water washed to remove any methanol which is also harmful to a cold acid alkylation process. The $C_4$ overheads or raffinate containing the normal butenes can be used in a cold acid alkylation process.

The temperature in each reaction distillation zone is dependent upon the pressure within the vessel. An overhead pressure of between 100 and 110 psig is preferred and provides a reaction temperature in the etherification zone of between 90 and 175° F. and a temperature within the hydrogenation zone of between 85° and 170° F.

EXAMPLE

A reactor system was configured as shown in the FIG. 1. The catalytic distillation (CD) column reactor comprised a stripping section of fifty feet packed with pall rings. The diameter of the stripping section was four inches below the feed point and three inches above the feed point. The vapor from the stripping section was passed to a three inch diameter reaction zone having the two beds of catalytic distillation structure. The lower twenty feet of the reaction zone was packed with acid cation exchange resin catalyst in the cloth bags as described. The feed point for the CD reactor was below the resin catalyst. Directly above the etherification catalyst the column was packed with twenty five feet of the palladium on alumina catalyst in wire mesh containers as previously described. The liquid from the reaction section (the middle reflux) was passed directly down to the stripping section with a sample being taken and analyzed by IR for methanol content.

The hydrocarbon feed to the guard bed reactor was $C_4$ FCC. The isobutene concentration averaged 12–13 wt. %. Butadiene in the feed concentration averaged 0.5 wt. % (about 0.3–0.6 wt. %). When higher concentrations were required as shown in FIG. 2 commercial grade 1,3-butadiene was added to the feed. FIG. 2 shows the effect of hydrogen feed rate on butadiene conversion at various levels of butadiene concentration. Hydrogen was technical grade purity (99.95% $H_2$). Mercaptans were less than 2 ppm and acetonitrile concentrations averaged 20 ppm. The methanol was 99.9% pure.

The column was operated at an overhead pressure of 110 psia. Methanol was fed to the unit to produce an azeotropic value of about 4 wt. % in the overhead after the hydrogenation catalyst had become activated.

The average overall isobutene conversion for the run in CD reactor etherification zone was greater than 90%. Average isobutene conversions based on MTBE yield and total isobutene fed to the unit are calculated to be 98.0%. FIG. 2 shows that the $C_4$ raffinate can be hydrogenated in the presence of methanol to less than 100 wppm butadiene from a feed gas stream containing up to 0.5 wt % (5000 wppm) butadiene. A typical run for the CD reactor is described in the following TABLE.

TABLE

| | | | | | | | | |
|---|---|---|---|---|---|---|---|---|
| HOURS ON STREAM | | | 446 | | | | 926 | |
| CONDITIONS PRESSURE, PSIA TEMP. °F. | | | 110 | | | | 110 | |
| BTMS | | | 285 | | | | 290 | |
| CAT. ZONE | | | | | | | | |
| (22) | | | 151 | | | | 156 | |
| (24) | | | 152–125 | | | | 154 | |
| OVERHEAD | | | 125 | | | | 142 | |
| STREAM | 103 | 105 | 107 | 108 | 103 | 105 | 107 | 108 |
| COMPOSITION, WT % | | | | | | | | |
| Methane | 0.000 | 0.000 | 0.000 | 0.000 | 0.000 | 0.000 | 0.000 | 0.061 |
| Ethane | 0.045 | 0.000 | 0.000 | 0.034 | 0.045 | 0.000 | 0.000 | 0.029 |
| Ethylene | 0.001 | 0.000 | 0.000 | 0.000 | 0.001 | 0.000 | 0.000 | 0.000 |
| Propane | 1.598 | 0.000 | 0.000 | 1.636 | 1.598 | 0.000 | 0.000 | 0.136 |
| Propylene | 0.080 | 0.000 | 0.000 | 0.073 | 0.080 | 0.000 | 0.000 | 0.013 |
| iso-Butane | 27.688 | 0.000 | 0.000 | 33.811 | 27.688 | 0.000 | 0.000 | 32.280 |
| iso-Butene | 5.291 | 0.000 | 0.000 | 0.107 | 5.291 | 0.000 | 0.008 | 0.500 |

TABLE-continued

| | | | | | | | | |
|---|---|---|---|---|---|---|---|---|
| 1-Butene | 12.204 | 0.000 | 0.003 | 4.135 | 12.204 | 0.000 | 0.000 | 4.447 |
| 1,3-Butadiene | 0.399 | 0.000 | 0.000 | 0.001 | 0.399 | 0.000 | 0.000 | 0.000 |
| n-Butane | 8.909 | 0.000 | 0.000 | 12.450 | 8.909 | 0.000 | 0.000 | 11.751 |
| trans-2-Butene | 15.490 | 0.000 | 0.000 | 31.810 | 15.490 | 0.000 | 0.000 | 31.521 |
| 2,2-Dimethyl-propane | 0.004 | 0.000 | 0.000 | 0.000 | 0.004 | 0.000 | 0.000 | 0.000 |
| Methyl-cyclopropane | 0.013 | 0.000 | 0.000 | 0.014 | 0.013 | 0.000 | 0.000 | 0.016 |
| cis-2-Butene | 11.749 | 0.000 | 0.000 | 14.407 | 11.749 | 0.000 | 0.000 | 15.247 |
| 3-Methyl-1-butene | 0.359 | 0.000 | 0.059 | 0.017 | 0.359 | 0.000 | 0.098 | 0.029 |
| iso-Pentane | 0.599 | 0.000 | 2.239 | 0.009 | 0.599 | 0.000 | 2.166 | 0.008 |
| 1-Pentene | 0.032 | 0.000 | 0.122 | 0.000 | 0.032 | 0.000 | 0.127 | 0.000 |
| 2-Methyl-1-butene | 0.016 | 0.000 | 0.029 | 0.013 | 0.016 | 0.000 | 0.041 | 0.014 |
| n-Pentane | 0.005 | 0.000 | 0.017 | 0.000 | 0.005 | 0.000 | 0.076 | 0.000 |
| 2-Methyl-1,3-butadiene | 0.003 | 0.000 | 0.003 | 0.000 | 0.003 | 0.000 | 0.004 | 0.000 |
| trans-2-Pentene | 0.011 | 0.000 | 0.037 | 0.000 | 0.011 | 0.000 | 0.030 | 0.000 |
| cis-2-Pentene | 0.004 | 0.000 | 0.015 | 0.000 | 0.004 | 0.000 | 0.013 | 0.000 |
| 2-Methyl-2-butene | 0.032 | 0.000 | 0.481 | 0.098 | 0.032 | 0.000 | 0.365 | 0.116 |
| trans-1,3-Pentadiene | 0.000 | 0.000 | 0.000 | 0.000 | 0.000 | 0.000 | 0.078 | 0.000 |
| cis-1,3-Pentadiene | 0.000 | 0.000 | 0.000 | 0.000 | 0.000 | 0.000 | 0.001 | 0.000 |
| Dimethyl-ether | 0.000 | 0.000 | 0.000 | 0.008 | 0.000 | 0.000 | 0.000 | 0.013 |
| Methenol | 2.855 | 0.000 | 0.000 | 1.103 | 2.855 | 0.000 | 0.007 | 3.725 |
| tert-Butanol | 0.000 | 0.000 | 0.098 | 0.000 | 0.000 | 0.000 | 0.000 | 0.000 |
| Methyl-tert-butyl-ether | 12.380 | 0.000 | 95.364 | 0.000 | 12.380 | 0.000 | 95.636 | 0.000 |
| Methyl-sec-butyl-ether | 0.015 | 0.000 | 0.203 | 0.000 | 0.015 | 0.000 | 0.085 | 0.000 |
| tert-Amyl-methyl-ether | 0.010 | 0.000 | 1.236 | 0.000 | 0.010 | 0.000 | 1.097 | 0.000 |
| DIB-1(2,4,4-Trimethyl- | 0.000 | 0.000 | 0.008 | 0.000 | 0.000 | 0.000 | 0.004 | 0.000 |
| DIB-2(2,4,5-Trimethyl- | 0.000 | 0.000 | 0.000 | 0.000 | 0.000 | 0.000 | 0.003 | 0.000 |
| Heavies | 0.209 | 0.000 | 0.048 | 0.271 | 0.209 | 0.000 | 0.111 | 0.095 |
| Unknowns | 0.002 | 0.000 | 0.039 | 0.003 | 0.002 | 0.000 | 0.050 | 0.000 |
| Flow, lb/hrs. | 120 | | 23.6 | 92.4 | 112.2 | | 24.7 | 91.6 |
| $H_2$ SCFH | | 30.1 | | | | 14.1 | | |

The invention claimed is:

1. A process for the production of alkyl tertiary alkyl ether and hydrogenation of the dienes contained in an isoalkene containing stream used for the etherification, comprising the steps of:
  (a) feeding a first stream containing isoalkene and diene, a second stream containing alcohol and a third stream containing hydrogen to a distillation column reactor into a feed zone;
  (b) contacting the streams in an etherification reaction distillation zone containing an etherification catalyst to:
    (i) selectively react at least a portion of the isoalkene with a portion of the alcohol to form alkyl tertiary alkyl ether,
    (ii) distill the alkyl tertiary alkyl ether downward out of the etherification reaction distillation zone and
    (iii) distill the unreacted isoalkene, alcohol, diene and hydrogen upward out of the etherification reaction distillation zone;
  (c) contacting the unreacted isoalkene, alcohol, diene and hydrogen in a hydrogenation reaction distillation zone containing a hydrogenation catalyst to selectively hydrogenate a portion of the dienes to alkenes;
  (d) withdrawing ether product from the distillation column reactor as bottoms; and
  (e) withdrawing an overheads stream from the distillation column reactor having a reduced diene content as compared to the diene content of the first stream.

2. The process according to claim 1 wherein said alkene has from four to six carbon atoms.

3. The process according to claim 1 wherein said alcohol is a monool having one to four carbon atoms.

4. The process according to claim 1 wherein said isoalkene comprises isobutene.

5. The process according to claim 4 wherein said alcohol is methanol, ethanol or a mixture thereof.

6. The process according to claim 1 wherein said isoalkene comprises isoamylenes.

7. The process according to claim 6 wherein said alcohol is methanol, ethanol or a mixture thereof.

8. A process for the production of methyl tertiary butyl ether and hydrogenation of the butadiene contained in the $C_4$ stream used for the etherification, comprising the steps of:
  (a) feeding a first stream containing isobutene and butadiene, a second stream containing methanol and a third stream containing hydrogen to a distillation column reactor into a feed zone;
  (b) contacting the streams in an etherification reaction distillation zone containing an etherification catalyst to
    (i) selectively react at least a portion of the isobutene with a portion of the methanol to form methyl tertiary butyl ether,
    (ii) distill the methyl tertiary butyl ether downward out of the etherification reaction distillation zone and
    (iii) distill the unreacted isobutene, methanol, butadiene and hydrogen upward out of the etherification reaction distillation zone;
  (c) contacting the unreacted isobutene, methanol, butadiene and hydrogen in hydrogenation reaction distillation zone containing a hydrogenation catalyst to selectively hydrogenate a portion of the butadiene to butenes;
  (d) withdrawing ether product from the distillation column reactor as bottoms; and
  (e) withdrawing an overheads stream from the distillation column reactor having a reduced butadiene content as compared to the butadiene content of the first stream.

9. The process according to claim 8 wherein said first stream also contains normal butenes which are removed with the overheads from the distillation column reactor.

10. The process according to claim 8 wherein the butadiene level in the overhead stream is reduced to 100 weight parts per million or less.

11. The process according to claim 8 wherein the ether product is stripped of any unreacted methanol and $C_4$'s in a stripping section below the etherification reaction distillation zone in the distillation column reactor.

12. The process according to claim 11 wherein the methanol content of the ether product entering the stripping section is an azeotropic amount or less.

13. In a process for the production of methyl tertiary butyl ether using a $C_4$ stream from a fluid catalytic cracking unit in a distillation column reactor having an etherification reaction distillation zone, the improvement comprising placing a hydrogenation reaction distillation zone above the etherification reaction distillation zone to hydrogenate a portion of the butadiene contained in the $C_4$ stream.

14. The process according to claim 13 wherein the butadiene level in $C_4$ stream is reduced to 100 weight parts per million or less.

15. The process according to claim 13 wherein the etherification reaction distillation zone contains an acid cation exchange resin catalyst in the form of a catalytic distillation structure.

16. The process according to claim 13 wherein the hydrogenation reaction distillation zone contains an alumina supported palladium catalyst containing about 0.5 wt % palladium in the form of a catalytic distillation structure.

17. A process for the production of alkyl tertiary alkyl ether and hydrogenation of the dienes contained in an isoalkene containing stream used for the etherification, comprising the steps of:

(a) feeding a first stream containing alkyl tertiary alkyl ether isoalkene, diene and alcohol and a second stream containing hydrogen to a distillation column reactor into a feed zone;

(b) distilling the alkyl tertiary alkyl ether downward out of a distillation zone and (c) distilling the unreacted isoalkene, alcohol, diene and hydrogen upward out of said distillation zone;

(d) contacting the unreacted isoalkene, alcohol, diene and hydrogen in a hydrogenation reaction distillation zone containing a hydrogenation catalyst prepared as a distillation structure to selectively hydrogenate a portion of the dienes to alkenes;

(e) withdrawing ether product from the distillation column reactor as bottoms; and (f) withdrawing an overheads stream from the distillation column reactor having a reduced diene content as compared to the diene content of the first stream.

* * * * *